United States Patent [19]

Jasserand et al.

[11] Patent Number: 5,283,243
[45] Date of Patent: Feb. 1, 1994

[54] PIPERIDINOALKYLBENZOXAZINE AND PIPERIDINOALKYLBENZOTHIAZINE COMPOUNDS, AND MEDICAMENTS CONTAINING THEM

[75] Inventors: Daniel Jasserand, Lyon; Francois Floc', Limonest; Richard White, Bourg en Bresse, all of France

[73] Assignee: Kali-Chemie Pharma GmbH, Hanover, Fed. Rep. of Germany

[21] Appl. No.: 792,425

[22] Filed: Nov. 15, 1991

[30] Foreign Application Priority Data

Nov. 24, 1990 [DE] Fed. Rep. of Germany ....... 4037426

[51] Int. Cl.$^5$ ................. C07D 265/36; C07D 279/16; A61K 31/54; A61K 31/535
[52] U.S. Cl. ................. 514/224.5; 544/52; 544/32; 544/101; 544/105; 514/224.2; 514/229.8; 514/230.5
[58] Field of Search ............. 514/224.5, 224.2, 229.8, 514/230.5; 544/52, 32, 101, 105

[56] References Cited

U.S. PATENT DOCUMENTS

| | | | |
|---|---|---|---|
| 4,640,916 | 2/1987 | Meguro et al. | 514/222 |
| 4,680,296 | 7/1987 | Manoury et al. | 514/259 |
| 4,760,074 | 7/1988 | Janssens et al. | 514/303 |
| 4,789,675 | 12/1988 | Meguro et al. | 514/229.8 |
| 4,820,822 | 4/1989 | Janssens et al. | 546/118 |

FOREIGN PATENT DOCUMENTS 233728 8/1987 European Pat. Off. .

OTHER PUBLICATIONS

Cossent et al. Chemical Abstracts 106(5):33092s (1987).

Janssens et al., *J. Med. Chem.*, vol. 28, pp. 1934–1943 (1985).

*Primary Examiner*—John M. Ford
*Attorney, Agent, or Firm*—Evenson, McKeown, Edwards & Lenahan

[57] ABSTRACT

Pharmacologically active compounds corresponding to the formula I

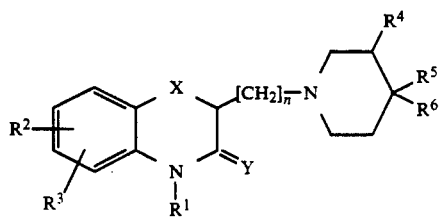

which are optionally substituted in the benzene ring and in which
X denotes oxygen or sulfur,
Y denotes oxygen or sulfur,
$R^1$ denotes hydrogen or lower alkyl,
n is an integer from 0 to 4,
$R^4$ denotes hydrogen, and
$R^5$ denotes hydrogen, hydroxy or cyano, or
$R^4$ and $R^5$ together form a bond,
$R^6$ denotes an A—$R^7$ group in which $R^7$ denotes an optionally substituted phenyl group, and A denotes a —$CH_2$— group, a CO group or a bond, or
$R^6$ is a halogen-substituted 1-phenylmethyl-1H-benzimidazol-2-ylamino group, and physiologically acceptable acid addition salts thereof.

9 Claims, No Drawings

PIPERIDINOALKYLBENZOXAZINE AND PIPERIDINOALKYLBENZOTHIAZINE COMPOUNDS, AND MEDICAMENTS CONTAINING THEM

BACKGROUND OF THE INVENTION

The present invention relates to novel benzoxazine-3-one and benzothiazine-3-one derivatives carrying a substituted piperidinoalkyl radical in the 2-position, and the corresponding 3-thione derivatives and salts thereof; to pharmaceutical compositions containing such compounds, and to processes for preparing such compounds.

1,4-Benzoxazine-3-one derivatives which carry a phenylpiperazinoalkyl group in the 2-position are known from published European patent application No. EP 233,728. These compounds have pronounced hypotensive and vasodilating effects.

SUMMARY OF THE INVENTION

It is the object of the present invention to provide new pharmaceutically active compounds which can be used as anti-allergic agents.

Another object of the invention is to provide new benzoxazine derivatives having valuable pharmacological properties.

These and other objects of the invention are achieved by providing a compound corresponding to the formula I

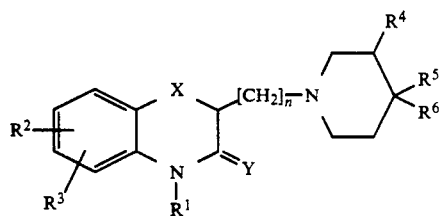

wherein

X denotes oxygen or sulfur,

Y denotes oxygen or sulfur, $R^1$ denotes hydrogen or lower alkyl, $R^2$ denotes hydrogen, lower alkyl, halogen, lower alkoxy, hydroxy, nitro or trifluoromethyl, and $R^3$ denotes hydrogen, lower alkyl, halogen or lower alkoxy, or $R^2$ and $R^3$ are bonded to adjacent carbon atoms and together denote an alkylenedioxy group having 1-2 carbon atoms, n is an integer from 0 to 4, $R^4$ denotes hydrogen, and $R^5$ denotes hydrogen, hydroxy or cyano, or $R^4$ and $R^5$ together form a bond, $R^6$ denotes an A—$R^7$ group, wherein $R^7$ denotes a phenyl group substituted by 0 to 3 substituents selected from the group consisting of lower alkyl, lower alkoxy, halogen and trifluoromethyl, and A denotes a —$CH_2$— group, a CO group or a bond, or $R^6$ denotes a group corresponding to the formula a

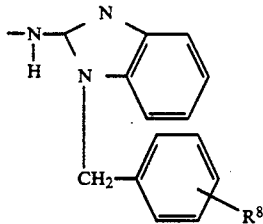

wherein $R^8$ denotes halogen, and physiologically acceptable acid addition salts thereof According to a further aspect of the invention, the objects are achieved by providing a pharmaceutical composition comprising an effective anti-inflammatory or anti-allergic amount of a compound as described above and at least one conventional pharmaceutical adjuvant.

In accordance with another aspect of the invention, the objects are achieved by providing a process for preparing a compound corresponding to the formula I

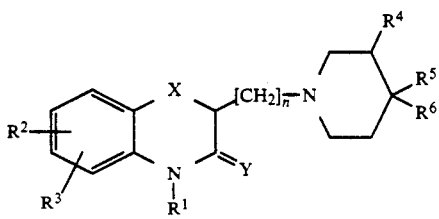

wherein

X denotes oxygen or sulfur,

Y denotes oxygen or sulfur, $R^1$ denotes hydrogen or lower alkyl, $R^2$ denotes hydrogen, lower alkyl, halogen, lower alkoxy, hydroxy, nitro or trifluoromethyl, and $R^3$ denotes hydrogen, lower alkyl, halogen or lower alkoxy, or $R^2$ and $R^3$ are bonded to adjacent carbon atoms and together denote an alkylenedioxy group having 1-2 carbon atoms, n is an integer from 0 to 4, $R^4$ denotes hydrogen, and $R^5$ denotes hydrogen, hydroxy or cyano, or $R^4$ and $R^5$ together form a bond, $R^6$ denotes an A—$R^7$ group, wherein $R^7$ denotes a phenyl group substituted by 0 to 3 substituents selected from the group consisting of lower alkyl, lower alkoxy, halogen and trifluoromethyl, and A denotes a —$CH_2$— group, a CO group or a bond, or $R^6$ denotes a group corresponding to the formula a

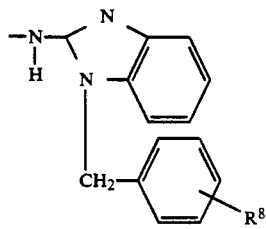

wherein R⁸ denotes halogen,
and acid addition salts thereof,
said process comprising:
 a) to prepare a compound corresponding to the formula Ia

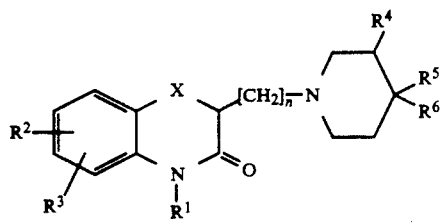

wherein X, R¹, R², R³, n, R⁴, R⁵ and R⁶ have the above meanings,
reacting a compound corresponding to the formula II

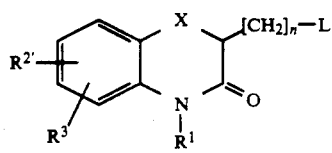

wherein
X, R¹, R² and n have the above meanings, and
R²′ has the meaning given for R² except that any hydroxy group is protected by a subsequently removable protective group, and
L denotes an aminolytically cleavable group, with a compound corresponding to the formula III

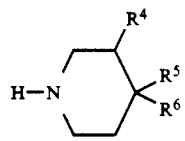

wherein R⁴, R⁵ and R⁶ have the above meanings, and thereafter removing any hydroxy protective group, or
 b) converting a compound corresponding to the formula Ia to a compound corresponding to the formula Ib

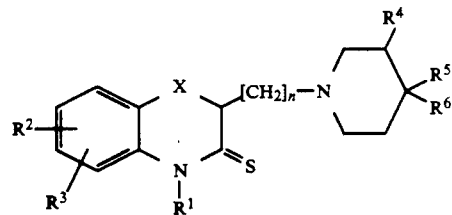

wherein X, R¹, R², R³, n, R⁴, R⁵, and R⁶ and have the above meanings.

DETAILED DESCRIPTION OF PREFERRED EMBODIMENTS

The novel heterocyclically substituted compounds of the invention have been found to have valuable pharmacological properties, to show anti-inflammatory and anti-allergic effects, and to have an advantageous activity profile with low toxicity and good tolerance. Due to their activity profile, the compounds of the invention are suitable for use as anti-inflammatory active ingredients and anti-allergic agents in the treatment of inflammatory and allergic diseases.

The present invention therefore relates to novel compounds of the general formula I

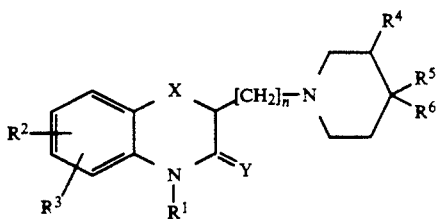

in which
X denotes oxygen or sulfur,
Y denotes oxygen or sulfur,
R¹ denotes hydrogen or lower alkyl,
R² denotes hydrogen, lower alkyl, halogen, lower alkoxy, hydroxy, nitro, or trifluoromethyl, and
R³ denotes hydrogen, lower alkyl, halogen or lower alkoxy, or
R² and R³ are bonded to adjacent carbon atoms and together denote an alkylenedioxy group having 1–2 carbon atoms,
n is a whole number from 0 to 4,
R⁴ denotes hydrogen, and
R⁵ denotes hydrogen, hydroxy or cyano, or
R⁴ and R⁵ together form a bond,
R⁶ is an A—R⁷ group, wherein R⁷ denotes a phenyl group optionally substituted by 1–3 substituents selected from the group consisting of lower alkyl, lower alkoxy, halogen and trifluoromethyl, and A denotes a —CH₂— group, a CO group or a bond, or
R⁶ is a group corresponding to the formula "a"

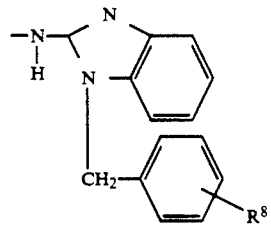

wherein R⁸ denotes halogen,
and physiologically acceptable acid addition salts thereof.

In so far as the substituents R² and R³ in the compounds of formula I and the substituents in the group R⁶ represent or contain lower alkyl groups, these may be straight chain or branched and contain in particular 1–4, preferably 1–2, carbon atoms and represent in particular methyl or methoxy. In so far as the substituents represent halogen, they may be fluorine, chlorine or bromine, preferably chlorine. The benzene ring of the ring structure may advantageously be unsubstituted. In so far as the benzene ring is substituted by a substituent R², or by two substituents R² and R³, lower alkyl substituents, for example methyl substituents, are considered particularly suitable.

The substituent R¹ advantageously represents hydrogen. If R¹ is lower alkyl, it may be straight-chain or branched and may contain 1-4, in particular 1-2, carbon atoms.

In the compounds of formula I, n represents 0-4. An alkylene chain having 3 or 4 members has proved to be particularly advantageous.

The substituents $R^4$ and $R^5$ on the piperidine ring may be hydrogen. However, $R^4$ and $R^5$ together may also form a bond, or $R^5$ may be hydroxy or cyano.

The substituent $R^6$ may be a group $A-R^7$ or a group "a". In the group $A-R^7$ A represents a methylene group or a bond. A may also represent a CO group. $R^7$ is preferably an unsubstituted phenyl group or optionally a phenyl group substituted by lower alkoxy, lower alkyl or halogen. A benzyl group $R^6$ optionally substituted by lower alkyl has proved to be particularly advantageous. In so far as $R^6$ represents a group "a", the halogen substituent $R^8$ thereof may in particular be fluorine, chlorine or bromine, preferably fluorine. $R^8$ is preferably situated in the 4-position of the benzyl group.

In accordance with the invention, the novel compounds of formula I and their acid addition salts are obtained in a known manner by a) to prepare compounds of the general formula Ia

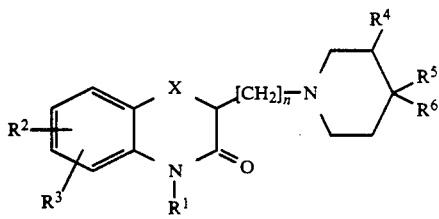

in which X, $R^1$, $R^2$, $R^3$, n, $R^4$, $R^5$ and $R^6$ have the above meanings,
reacting compounds of the general formula II

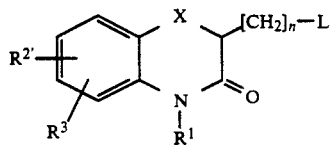

in which
X, $R^1$, $R^3$ and n have the above meanings, and
$R^{2'}$ has the meaning given for $R^2$, except that any hydroxy group is protected by a subsequently removable protective group, and
L is an aminolytically cleavable group,
with compounds of the general formula III

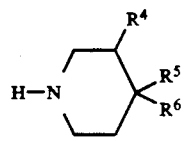

in which $R^4$, $R^5$ and $R^6$ have the above meanings, and subsequently removing any hydroxy protective group, or b) converting compounds of the general formula Ia to compounds of the general formula Ib

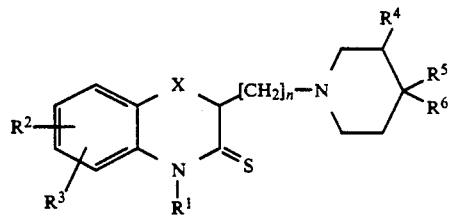

wherein X, $R^1$, $R^2$, $R^3$, n, $R^4$, $R^5$ and $R^6$ have the above meanings, and optionally in compounds of the general formula I which are obtained in which $R^1$ denotes hydrogen, alkylating to form compounds of the general formula I in which $R^1$ denotes lower alkyl, and/or optionally in compounds of the general formula I which are obtained in which $R^2$ denotes methoxy, cleaving the methoxy group to form a hydroxy group, and/or optionally converting free compounds of formula I which are obtained into their acid addition salts or converting acid addition salts which are obtained into the free compounds of formula I.

The reaction of compounds of formula II with compounds of formula III according to process variant a) may be carried out by conventional methods for alkylating amines.

The reaction is advantageously carried out under basic conditions in an organic solvent which is inert under the reaction conditions.

Halogens, such as chlorine, bromine or iodine, preferably bromine or chlorine, or an acyloxy radical O-Z in which Z represents a lower alkanoyl radical or an organic sulfonic acid radical, for example the residue of a lower alkanesulfonic acid such as, for example, methanesulfonic acid, or of an aromatic sulfonic acid such as benzenesulfonic acid or benzenesulfonic acids substituted by lower alkyl or by halogen, for example toluenesulfonic acids or bromobenzenesulfonic acids, are suitable as aminolytically cleavable groups L in the compounds of formula II. Aprotic solvents, for example aromatic hydrocarbons such as toluene, xylene or benzene, cyclic ethers such as dioxane, dimethylformamide, lower alkanols such as ethanol, or mixtures of the aforementioned solvents are particularly suitable as inert organic solvents.

The process is advantageously carried out at elevated temperatures, for example temperatures between 50° and 150° C., preferably the reflux temperature of the solvent.

The reaction is advantageously carried out with addition of an organic or inorganic base. However, an excess of the compound of the formula III may also be used, and this may serve as an internal base. Examples of suitable organic bases include tertiary organic amines, particularly tertiary lower alkyl amines such as triethylamine, tripropylamine, N-lower alkyl morpholines or N-lower alkyl piperidines. Suitable inorganic bases include in particular alkali metal carbonates or alkali metal bicarbonates.

The reaction time may be between 2 and 8 hours depending on the reaction conditions. Known ether protective groups which can subsequently be removed in a known manner solvolytically or hydrogenolytically, for example lower alkyl or benzyl groups, may be selected as protective groups for any hydroxy group $R^2$.

The conversion of the 3-one group of the compounds of formula Ia into the 3-thione group of the compounds of formula Ib according to process variant b) may be carried out by conventional methods for exchanging oxygen for sulfur in oxo compounds. Thus, the compounds of formula Ib may be prepared in a known manner, for example by treating the compounds of formula Ia with a phosphorus pentasulfide (for example $P_4S_{10}$), or also according to the method described by Lawesson et al. (see Bull. Soc. Chim. Belg. 87, 525–534 (1978)) by reacting the compound Ia with 2,4-bis(methoxyphenyl)-1,3-dithia-2,4-diphosphetane-2,4-disulfide of the formula IV

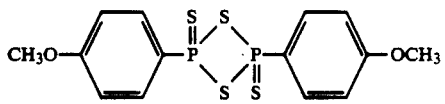

(=known as Lawesson's reagent). The deoxosulfurization is advantageously carried out in an organic solvent which is inert under the reaction conditions, for example an aromatic hydrocarbon such as xylene or toluene, at elevated temperatures, for example temperatures between 50° and 150° C., preferably at the reflux temperature of the reaction mixture. When the reaction is completed the sulfurized compounds may be separated from the phosphorus derivatives by filtration.

If desired, compounds of formula I which are obtained in which $R^1$ denotes hydrogen optionally may be subsequently alkylated in a known manner to form the corresponding N-alkyl compounds. Suitable alkylating agents include alkyl halides, particularly iodides, alkyl sulfates or alkyl sulfonates. A compound of formula I containing an amide or thiamide group is advantageously reacted initially with a strong base, such as for example an alkali metal hydride, alkali metal amide or alkali metal alcoholate, in an inert polar organic solvent and then further reacted with the alkylating agent. The reaction may be carried out at a temperature from 0° C. up to the reflux temperature of the solvent. Dimethylformamide or cyclic ethers, such as tetrahydrofuran or dioxane, are suitable as solvents depending on the metalation agent used, or, if the base is a metal alcoholate, also the corresponding alcohols. Thus, for example, the reaction may advantageously be carried out in dimethylformamide using sodium hydride.

In compounds of formula I in which $R^2$ denotes methoxy, the methoxy group may be cleaved to form a hydroxy group in a known manner using methods suitable for cleaving methoxyaryl ethers. For example, the ether may be cleaved by treating it with hydrogen iodide in a solvent which is inert under the reaction conditions, for example acetanhydride, or with iodotrimethylsilane or boron tribromide.

The compounds of the formula I can be isolated from the reaction mixture and purified in a known manner. Acid addition salts may be converted in conventional manner to the free bases, and if desired, the free bases may be converted in known manner to pharmacologically acceptable acid addition salts.

Suitable pharmacologically acceptable acid addition salts of the compounds of formula I include, for example their salts with inorganic acids, for example hydrohalic acids, particularly hydrochloric acid, sulfuric acid or phosphoric acids, or with organic acids, for example lower aliphatic monocarboxylic or dicarboxylic acids, such as maleic acid, fumaric acid, lactic acid, tartaric acid or acetic acid, or sulfonic acids, for example lower alkyl sulfonic acids such as methanesulfonic acid, or benzenesulfonic acids optionally substituted in the benzene ring by halogen or lower alkyl, such as p-toluenesulfonic acid, or cyclohexylaminesulfonic acid.

The compounds of the formula I contain an asymmetric center in the 2-position of the benzoxazine or benzothiazine structure and may exist in two optically active enantiomeric forms or as a racemate. The present invention includes both the racemic mixtures as well as the pure optical isomers of the compounds of formula I.

If racemates of compounds of formula II or formula IV are used in the synthesis, the resulting compounds of formula I are obtained in the form of racemates. Optically active compounds corresponding to formula I may be obtained starting from optically active forms of compounds of formula II or formula IV. Optically active compounds of formula I may be isolated from racemic mixtures in a known manner, for example by chromatographic separation on chiral separating materials or by reacting with suitable optically active acids, for example tartaric acid or 10-camphorsulfonic acid, and then separating the resulting salts into their optically active antipodes by fractional crystallization.

The starting compounds of formula II may be obtained starting from 2-aminophenol derivatives corresponding to the formula V

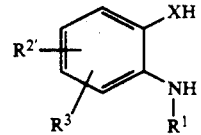

in which $R^1$, $R^2$, $R^3$ and X have the above meanings.

Accordingly, the compounds of formula V may be condensed in a known manner with a β-bromo-acylbromide corresponding to the formula VI

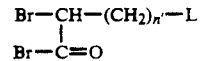

in which L has the above meaning, and n' denotes 1–4, to form compounds of the formula IIa

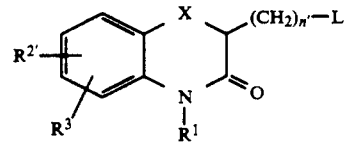

in which $R^1$, $R^{2'}$, $R^3$, X, n' and L have the above meanings. The condensation may be carried out in a solvent which is inert under the reaction conditions, for example a halogenated hydrocarbon such as chloroform, in the presence of a base, for example an alkali metal hydrogen carbonate or alkali metal carbonate, and is advantageously carried out in the presence of a transfer catalyst, for example benzyltrimethylammonium chloride. The compounds of the formula V can also be reacted in a known manner with β-bromoalkanecarboxylic acid methyl esters of the formula VII

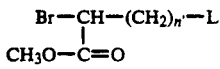

in which n' and L have the above meanings, to form compounds of the formula IIa. The reaction may, for example, be carried out in dimethylformamide in the presence of an inorganic base, for example an alkali metal carbonate. Compounds of the general formula Va

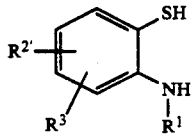

in which $R^1$, $R^{2'}$ and $R^3$ have the above meanings, are known or may be obtained in a known manner starting from compounds of the general formula IX

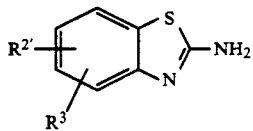

in which $R^{2'}$ and $R^3$ have the above meanings. Compounds of the formula IX may be alkylated to introduce an alkyl group $R^1$ in a known manner to form compounds of the general formula X

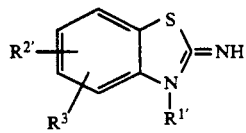

in which $R^{2*}$ and $R^3$ have the above meanings, and $R^{1'}$ denotes lower alkyl.

Compounds of formula IX or formula X may be converted to compounds of formula Va in a known manner by thermal dissociation in an aqueous alkaline medium, for example by heating in alkali metal hydroxide solution.

Compounds of the general formula Vb

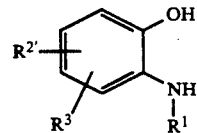

in which $R^1$, $R^{2'}$ and $R^3$ have the above meanings, are known or may be obtained by known methods or analogously to known methods. 2-Alkylaminophenol compounds ($R^1$=lower alkyl) may be obtained starting from the corresponding 2-aminophenol compounds. For this purpose they are initially acylated, whereby both the phenolic hydroxy group and the amino group are provided with a protective acyl group. The amide group in the resulting ester-amide compounds is alkylated in a known manner by reacting the compounds with an alkylating agent, for example a lower alkyl halide, alkyl sulfate or alkyl sulfonate, in the presence of a strong base, for example an alkali metal hydride or alkali metal hydroxide, optionally in the presence of a transfer catalyst, for example benzyltrimethylammonium chloride. The reaction may take place, for example under the conditions given above for the subsequent alkylation of compounds of the formula I. After the alkylation is completed, the protective acyl groups may then be removed in a known manner by acid or alkaline hydrolysis.

Compounds of formula II in which n denotes 0, may be obtained starting from compounds of the formula VIII

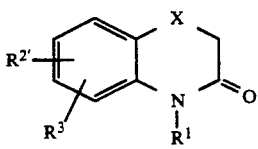

in which $R^1$, $R^{2'}$, $R^3$ and X have the above meanings. Hence, prepare compounds of the formula IIb

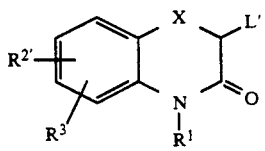

in which $R^1$, $R^{2'}$ and $R^3$ have the above meanings, and L' denotes halogen, a halogen substituent L', particularly chlorine, can be introduced into compounds of the formula VIII in a known manner by treatment with a halogenating agent, for example sulfuryl chloride. The chlorination may be carried out in a solvent which is inert under the reaction conditions, for example a halogenated hydrocarbon such as dichloromethane.

Compounds of formula VIII are known or may be obtained in a known manner, for example by condensing compounds of formula V with chloroacetyl chloride. The condensation may be carried out under the reaction conditions given above for preparing compounds of formula IIa.

Compounds of formula III are known or may be prepared by, or analogously to, known methods. Hence, compounds of formula III may be obtained, for example, starting from piperidone compounds of the general formula XI

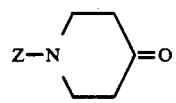

in which Z denotes an amino protective group. For this purpose the aldehydes of formula XI are initially reacted in a Grignard reaction with a Grignard reagent of the general formula XII

in which $R^6$ and L' have the above meanings, to form the alcohols of the general formula XIII

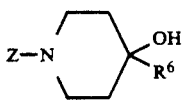

in which R$^6$ and Z have the above meanings, and compounds of formula III in which R$^5$ denotes hydroxy are obtained from these alcohols by removing the amino protective group. Compounds of formula III in which R$^4$ and R$^5$ together represent a bond are obtained by eliminating water and removing the amino protective group from the compounds of formula XIII. Compounds of formula III in which R$^5$ denotes hydrogen are obtained by reducing the alcohols of formula XIII, for example by catalytic or chemical hydrogenolysis, and in appropriate cases simultaneously removing the amino protective group. To prepare compounds of formula III in which R$^5$ denotes cyano, the hydroxy group of the compounds of formula XIII initially is converted to halogen in a known manner by reacting with a halogenating agent, and the halogen is then converted to the cyano group by reacting with a cyanide compound.

To prepare the compounds of formula III in which R$^6$ is a CO-R$^7$ group, piperidine carboxylic acid halides of the general formula XIV

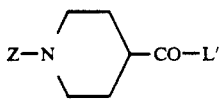

in which Z and L' have the above meanings, also may be initially reacted with compounds of the general formula XV

in which R$^7$ has the above meaning, in a Friedel-Crafts reaction in the presence of aluminium chloride to form ketones of the general formula XVI

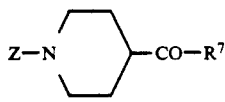

in which Z and R$^7$ have the above meanings, and the amino protective group may subsequently be removed from these ketones.

To prepare compounds of formula III in which R$^6$ is a group "a", compounds of the general formula XVII

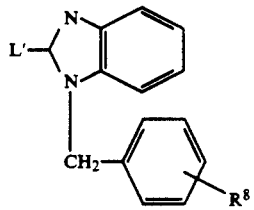

in which L' and R$^8$ have the above meanings, also may be reacted with an amino compound of the general formula XVIII

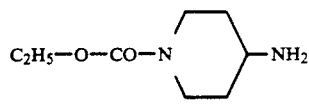

and the ethoxycarbonyl protective group may subsequently be removed.

The compounds of formula I and their pharmacologically acceptable acid addition salts are characterized by interesting pharmacological properties and have anti-inflammatory and anti-allergic effects. In particular, the compounds exhibit an advantageous activity profile for treating asthmatic disorders with low toxicity and good compatibility.

Asthma is a chronic inflammatory lung disease which is characterized by an episodic, reversible obstruction of the respiratory passages. It is generally assumed that the initiation of asthmatic symptoms and attacks stems from a parenchymal and interstitial cell type known as a mast cell. These mast cells contain pre-formed inflammation mediators and spasmogens, in particular histamine. They are also capable of synthesizing a variety of mediators derived from membrane lipids. Mast cells also act in conjunction with a number of associated cells which are all capable of synthesizing inflammatory and pro-inflammatory mediators.

As long as no allergy-inducing conditions are present, the mast cells are in a quasi dormant waiting state. The key to allergic reactions lies in the presence of high concentrations of circulating IgE antibodies. When these antibodies bind to a corresponding antigen, they activate both the degranulation and release of pre-formed mediators as well as the synthesis of other mediators.

Since asthma is an inflammatory obstructive lung disease, the therapy is based on essentially two approaches: alleviating the symptomatic complaints by administering bronchodilators such as β-sympathicomimetic agents, xanthine derivatives and anti-cholinergic agents; administration of anti-inflammatory active ingredients such as disodium cromoglycinate and steroids; and targeted therapy directed at specific mediators such as histamine, for example. Treatment to alleviate the symptomatic complaints is adequate in about 50% of asthmatics, but does not contribute anything to alleviating the cause, i.e. the inflammation. Anti-inflammatory active ingredients may control the inflammation, but often have undesirable side-effects and are frequently administered simultaneously with bronchodilators. Targeted therapy directed at a specific mediator alone is totally inadequate, since there are plethora of mediators.

The compounds of the invention are distinguished in that they have an anti-inflammatory effect and act in targeted fashion against one or more of the three types of mediators: histamine, leucotrienes and blood platelet aggregating factor, which contribute not only to acute bronchospasms but also to maintenance of chronic inflammation, or are also active against the respective target cells via mediator-specific receptors.

The anti-inflammatory and anti-allergic properties of the compounds of the invention can be demonstrated in vitro and in vivo by standard pharmacological test methods.

DESCRIPTION OF THE TEST METHODS

1. Determining Inhibition of Passive Cutaneous Anaphylaxis (PCA) and Histamine-Induced Anaphylactoid Cutaneous Reaction The PCA reaction is carried out following the methods described by Goose et al. (J.N. Immunology 16 (1969), 749) and by Martin et al. (Arch. Pharmacol. 316 (1981), 186).

The IgE-rich ovalbumin antiserum used in the test was obtained from immunized Brown-Norway rats. The were immunized with an intraperitoneal injection of a mixture of 100 μg of ovalbumin with a Bordetella pertussis suspension (Vaxicoq TM, Manufactured by Institute Merieux, containing $5 \times 10^9$ organisms and 1.25 mg $Al(OH)_3$). After 20 days the animals were re-immunized with a further intraperitoneal injection of a solution of 10 μg ovalbumin in 0.5 ml physiological saline solution. After a further four days the blood was removed from the animals and centrifuged. The resulting antiserum was stored at −20° C. until use.

The inhibition of the passive cutaneous anaphylaxis and of the anaphylactoid cutaneous reaction induced by histamine was determined as follows:

Sprague-Dawley rats having a body weight of 150–180 g were injected intradermally in one flank with 50 μl of a 1:75 dilution of the IgE-rich ovalbumin antiserum in physiological saline solution to passively sensitize them to ovalbumin.

24 hours after sensitization a solution of 8.25 mg/kg of ovalbumin and 26.4 mg/kg of a blue dye (Evans's Blue) was administered to the rats intravenously according to Martin et al. to trigger passive cutaneous anaphylaxis. The ovalbumin challenge resulted in a local anaphylactic reaction at the point where the antiserum was injected.

To determine the histamine-induced anaphylactoid skin reaction, the animals are injected intradermally in the flank opposite to the antiserum administration with 50 μl of a physiological saline solution containing 0.8 mg/ml histamine directly before the intravenous injection of the solution containing the ovalbumin and the blue dye.

On the day of the experiment the test substances were dissolved in distilled water which contained 1 vol. % dimethylformamide and 1 vol. % of Tween TM 20 (=polyoxyethylene (20) sorbitan monolaurate). One hour before administration of the ovalbumin challenge, each animal was orally administered $2 \times 10^{-5}$ mole/kg of test substance in 0.5 ml of solution. For comparison purposes a control group received only the solvent.

The edematous anaphylactic (PCA) and anaphylactoid (histamine-induced) reactions caused by the stimulation of the intravenous ovalbumin injection, which manifested themselves by edema formation, swelling and exudation of blue dye, were evaluated 30 minutes after their initiation by the intravenous ovalbumin injection. This was done by visually determining the extent to which the blue dye emerged at the sites of edema formation. The percentage inhibition of anaphylactic and anaphylactoid reactions induced by the test substances in comparison with the reactions of the control animals not treated with any test substance was determined using comparison scales.

The results obtained using compounds of formula I according to the foregoing test methods are shown in the following Table A. The example numbers given for the compounds of formula I relate to the subsequent preparative examples.

TABLE A

| Test Substance Example No. | Inhibiting effect on cutaneous anaphylactic and anaphylactoid reactions in Rats % inhibition by $2 \times 10^{-5}$ mole/kg dose per os | |
|---|---|---|
| | Passive cutaneous anaphylaxis (PCA) | Histamine-induced anaphylactoid reaction |
| 12 | 35 | 20 |
| 20 | 20 | 40 |
| 1 | 85 | 85 |
| 8 | 100 | 100 |
| 10 | 55 | 30 |
| 11 | 45 | 20 |
| 15 | 30 | 10 |
| 18 | 90 | 50 |

2. Determination of Minimum Toxic Dose

Maximum doses of 300 mg/kg of the test substance were administered orally to male mice weighing 20–25 g. The animals were observed carefully for 3 hours for toxicity symptoms. In addition, all symptoms and deaths were recorded over a period of 24 hours after administration. Associated symptoms were also observed and recorded. If death or severe toxic symptoms were observed, additional mice were administered increasingly lower doses. The lowest dose which produced death or severe toxic symptoms is given in the following Table B as the minimum toxic dose.

TABLE B

| Test substance Example No. | Minimum toxic dose mg/kg mouse per os |
|---|---|
| 3 | 300 |
| 4 | 300 |
| 8 | 300 |
| 10 | 300 |
| 15 | 300 |
| 16 | >300 |
| 21 | 100 |

3. Investigation of Anti-Histamine-($H_1$) Effect Based on Histamine-($H_1$)-Receptor Antagonism In Vitro To investigate the histamine-($H_1$)-receptor antagonism of the test substances, the inhibiting effect of the substances on histamine-induced contractions of the smooth muscle was determined in vitro on the isolated organ. Isolated strips of organ from the ileum are suitable for this purpose. In an organ bath of physiological saline solution the smooth muscle strips react to the addition of histamine by contracting. Addition of the compounds of the invention decreased the histamine-induced contraction of the smooth muscle of the ileum strips. The extent of regression of the contraction is an indication of the anti-histamine-($H_1$) activity of the compounds. The investigation was carried out analogously to the method originally described by Magnus (Pfluegers Arch. 102, 123 (1904)). Procedure for determining the smooth muscle contraction inhibiting effect on isolated guinea pig ileum induced by a $5 \times 10^{-6}$ molar histamine concentration.

Segments of the ileum 1.5 cm long from Dunkin Hartley guinea pigs having a body weight of 300 500 g were used for the test. Each strip was placed in an organ bath of 10 ml of physiological saline solution according to Krebs-Henseleit and attached to a conventional apparatus for isotonic measurement of changes in length of the ileum strips (automated Celaster measuring apparatus), so that the tissue was under 1 g of tension. The bath was kept at a pH of 7.4 and gassed with a mixture of 5% $CO_2$ and 95% $O_2$. After an equilibration phase, an isotonic contraction of the tissue was induced by adding histamine in a final concentration of $5 \times 10^{-6}$ mole/liter and washing it out again after a contact time of 30 seconds. Only tissues samples from which three reproducible contractions were obtained at 10 minute intervals were used in the subsequent test. The test substances were then added in a final concentration of $10^{-6}$ mole/liter, and after 30 seconds contact time histamine was again added up to a concentration of $5 \times 10^{-6}$ mole/liter. The resulting contractions were measured over 30 seconds. The tissue was then washed several times over a period of 10 minutes. Histamine was then added again to stimulate a contraction. The resulting contractions were again measured over 30 seconds. The difference between the amplitude of the contraction obtained by histamine addition alone and the amplitude of the contraction obtained in the presence of the test substance was determined and expressed in terms of % inhibition.

The following Table C shows the results obtained with the test substances according to the method described above. The inhibiting effects on the contractions induced by histamine 30 seconds after administration of the test substance and on the contractions induced by the addition of histamine 10 minutes later are listed in the table.

TABLE C

| Test Substance Example No. | in vitro ($H_1$)-receptor antagonism, % inhibition of histamine-induced ileum contractions at a histamine concentration of $5 \times 10^{-6}$ mole/l and a test substance concentration of $10^{-6}$ mole/l | |
|---|---|---|
| | after 30 seconds | after 10 minutes |
| 9 | 35 | 12 |
| 8 | 5 | 44 |
| 13 | 49 | 8 |

4. Determination of Anti-PAF Activity In Vitro

PAF (=Platelet Activating Factor) is a phospholipid mediator which has many effects. Activation of platelet aggregation induces protracted broncho-contraction and hyper-reactivity of the air paths.

In this test the effect of the test substances on platelet aggregation induced by adding PAF to a suspension of platelets obtained from rabbit blood is investigated using the method described by Mikashima et al. (Jap. J. Pharmacol. 44 (1987) 387-391).

A suspension of platelets obtained from rabbit blood containing $4 \times 10^9$ platelets/ml in a modified Tyrode buffer solution (=Tyrode solution with 1.3 mM/l $CaCl_2$ and 2.5 g/l gelatine added) adjusted to pH 7.4 was used. Tyrode solution is an aqueous solution containing 136.9 mmoles NaCl, 2.68 mmoles KCl, 2.31 mmoles $CaCl_2$, 1.0 mmole $MgCl_2$, 11.9 mmoles $NaHCO_3$, 1.45 mmoles $NaH_2PO_4$ and 5.55 mmoles glucose per liter. The platelets were obtained from 10 ml blood samples from each of three rabbits (New Zealand hybrids, body weight 3-4 kg). For this the blood samples were treated with ethylenediamine tetraacetic acid and washed according to the method of Artley et al. (Brit. J. Hematol. 19 (1970), 7-17). A platelet-rich plasma was then initially separated by centrifuging (20 minutes at $400 \times g$). The blood platelets were separated from the plasma by recentrifuging for 15 minutes at $1,400 \times g$. The platelets remaining as sediment after centrifuging were resuspended in a Tyrode buffer solution (but without calcium). 0.4 mmole of lysine acetylsalicylate was then added, and after 15 minutes the platelets were sedimented again. The sediment was resuspended in the aforementioned modified Tyrode buffer solution, and the number of platelets in the resulting suspension was adjusted to the desired content.

A $40 \times 10^{-9}$ molar PAF solution was used as a reagent. This solution was made from a $1.8 \times 10^{-3}$ molar stock solution in chloroform. For this purpose a 10 μl sample of the stock solution was evaporated to dryness and redissolved in 180 μl of the modified Tyrode solution to which 0.25% of lipid-free bovine serum albumin had been added. From this $10^{-5}$ molar working solutions were then prepared and stored frozen. Samples of these solutions were appropriately diluted for the tests.

To carry out the test 50 μl of the platelet suspension and 10 μl of a $40 \times 10^{-5}$ molar solution of the compound being investigated were added with stirring (1,000 rpm) to 330 μl of the modified Tyrode buffer solution in an aggregation tube provided with a small magnetic stirrer. This corresponds to a final test substance concentration of $10^{-5}$ mole/l. After 90 seconds preincubation time, 10 μl of the PAF preparation were added. The aggregation occurring in the aggregation tubes was measured over 4-5 minutes with the aid of a computerized aggregometer.

The aggregation which occurred in test tubes containing only platelet suspension was evaluated as 0%, whereas the aggregation which occurred in test tubes containing platelet suspension and PAF preparation was evaluated as 100%. The aggregation which still occurred during the inhibition of the PAF induced platelet aggregation due to the addition of the test substances was measured, and the resulting aggregation inhibition was calculated therefrom in %.

The results obtained using the compounds of formula I according to the foregoing method are shown in the following Table D.

TABLE D

| Test Substance Example No. | Anti-PAF activity in vitro % inhibition of the PAF-induced aggregation of rabbit blood platelets at a test substance concentration of $10^{-5}$ mole/l |
|---|---|
| 14 | 57 |
| 21 | 33 |
| 19 | 72 |

5. In vitro Determination of Cyclooxygenase Inhibition and 5-Lipoxygenase Inhibition After a cell is activated, arachidonic acid contained in cell membranes is metabolized in two ways. Leucotrienes, inter alia leucotriene $C_4$, are formed due to the action of the enzyme 5-lipoxyqenase (=5-LO), and prostanoids are formed due to the action of the enzyme cyclooxygenase (=CO). In in vitro systems these metabolites are secreted from the cell.

To evaluate the cyclooxygenase-inhibiting and 5-lipoxygenase-inhibiting properties of the test substances, their inhibitory activity on the biosynthesis of the arachidonic acid derivatives leucotriene $C_4$ (=$LTC_4$) and 6-keto-prostaglandin $F_{1\alpha}$ (=6-keto-$PGF_{1\alpha}$) was determined in vitro on mouse peritoneal macrophage cells. For this purpose the $LTC_4$ and 6-keto-$PGF_{1\alpha}$ contents of a mouse peritoneal macrophage cell culture medium were determined by zymosan stimulation as described by Scott et al. (J. Exp. Med.

152 (1980), 324–335) and by Fradin et al., (Prostaglandins, 33 (1987), 579–589).

A cell suspension containing peritoneal cells from male mice 8–10 weeks old was obtained in a known manner. A solution marketed under the designation RPMI 1640 (Manufactured by Gibco) was used as the cell culture medium, to which heparin (10 international units/ml) and antibiotics were added according to the procedure of Bonney et al. (Biochem. J. 176 (1978) 422–433). The cell suspension was adjusted to a cell concentration of $10^6$ cells per ml and distributed uniformly on titer dishes containing 24 1-ml titer cells (wells). These were kept for two hours in a humidified incubator filled with air enriched with 7% $CO_2$. Cells not adhering to the titer well walls were then removed by washing. The remaining macrophage cells adhering to the walls were incubated for about 12 hours in a suspension medium to which 0.1% of bovine serum albumin (BSA=Bovine Serum Albumin) was added. The suspension medium was then replaced by a Hanks salt solution (=Hanks Balanced Salt Solution=HBSS) with 10 mmoles of Hepes (=hydroxyethylpiperazinoethanesulfonic acid) to which a 0.1% strength solution of the test substances in aqueous, 1% strength dimethylformamide or only the solvent had been added. After 15 minutes the arachidonic acid metabolism was stimulated by adding 10 particles of zymosan (=glycoprotein mixture isolated from cell walls of beer yeast, Saccharomyces cerevisiae, Manufactured by Sigma Chemical Co., Munich) per titre cell. After 2 hours samples of the respective supernatant liquid in each cell were examined for their 6-keto-$PGF_{1\alpha}$ and $LTC_4$ contents by an enzyme immunoassay (=EIA). This EIA is carried out following the method of Pradelles et al. (Analytical Chem. 57 (1985), 1170–1173). The determination of $LTC_4$ and the determination of 6-keto-$PGF_{1\alpha}$ were each carried out on suitable dilutions of the samples (1:50 to 1:250 for the $LTC_4$ determination and 1:250 to 1:1,250 for the 6-keto-$PGF_{1\alpha}$ determination) in comparison with a comparative scale. To determine the inhibiting effect of a $10^{-5}$ molar concentration of the compounds, the amounts of reference eicosanoid were determined, and the inhibiting effect was calculated therefrom in % inhibition compared to the measurements of the zymosan controls. The results obtained in this test are shown in the following Table E.

TABLE E

| Test Substance Example No. | In vitro % inhibition in zymosan-stimulated mouse peritoneal macrophage cells at a concentration of $10^{-5}$ mole/l upon release of | |
|---|---|---|
| | 6-keto-$PGF_{1\alpha}$ | $LTC_4$ |
| 14 | 25 | 10 |
| 2 | 13 | 54 |
| 21 | 11 | 24 |
| 16 | 70 | 97 |
| 1 | 52 | 87 |
| 8 | 40 | 40 |
| 10 | 30 | 37 |
| 3 | 17 | 16 |
| 4 | 71 | 0 |
| 19 | 16 | 57 |

Due to their activities described above, the compounds of formula I are useful as anti-inflammatory and anti-allergic medicaments for larger mammals, in particular humans, for treating inflammatory and allergic diseases. The orally active compounds of the invention may act in several ways, since they are active against several of the principal mediators implicated in inflammatory processes and asthmatic complaints.

As a result of this activity profile it can be assumed that in the treatment of allergy-based and non-allergy-based asthma symptoms, the compounds of the invention will not only alleviate the symptomatic complaints associated with asthmatic diseases, but also may reduce the associated inflammation.

The doses to be used may vary from individual to individual and of course will vary depending on the nature of the condition to be treated, the substance used, and the manner of administration. For example, parenteral formulations will generally contain less active substance than oral preparations. However, medicament forms having an active ingredient content of 10 to 250 mg per individual dose are generally suitable for administration to larger mammals, in particular humans.

As medicaments, the compounds of formula I may be contained with conventional pharmaceutical auxiliaries in galenic formulations such as, for example, tablets, capsules, suppositories, or solutions. These galenic formulations may be produced by known methods using conventional solid carriers such as, for example, lactose, starch or talcum, or liquid paraffins, and using conventional pharmaceutical auxiliaries, for example, tablet disintegrating agents, solubility promoters or preservatives.

The following examples are intended to illustrate the invention in further detail without limiting its scope.

EXAMPLE 1

2-{4-[4-(N-(1-(4-fluorophenylmethyl)-1H-benzimidazol-2-yl)-amino)-piperidin-1-yl]-butyl}-2H-1,4-benzothiazine-3(4H)-one.

A) 45.3 g (=0.23 m) of 6-bromocaproic acid were treated with 63.6 g (=0.235 m) of phosphorus tribromide with stirring, and then 75.1 g (=0.047 m) of bromine were added, the first half being added dropwise and the remainder more rapidly. The mixture was then heated at a temperature of 85°–90° C. and maintained at this temperature for 1.5 hours. A further 18.4 g (=0.115 m) of bromine were added at this temperature, and the reaction mixture was maintained at a temperature of 85°–90° C. for a further 18 hours. The reaction mixture was worked up by cooling it to 20° C. and adding it to a mixture of 700 ml cooled water and 500 ml of cold hexane. The organic phase was separated, and the aqueous phase was washed two more times with 100 ml of hexane each time. The organic phases were combined and dried over sodium sulfate. The solvent was then distilled off. The 2,6-dibromocaproic acid bromide which remained as an oily residue was characterized by IR and NMR spectroscopy and further processed without additional purification.

B) 9.25 g (=0.07 m) of 2-aminothiophenol, 27.9 g of benzyltrimethylammonium chloride, and 25 g of sodium hydrogen carbonate were introduced into 150 ml of chloroform with stirring. The resulting suspension was cooled to −5° C., and a solution of 25.3 g of 2,6-dibromocaproic acid bromide in 70 ml of chloroform was added slowly with stirring to the cooled suspension. The addition took 30 minutes, and the temperature varied between −5° C. and +5° C. The mixture was maintained in this temperature range for a further hour. The mixture was then heated under reflux for 7 hours. Afterward it was cooled, filtered and the chloroform was distilled off from the filtrate. The remaining residue was treated with water and toluene. The organic phase was separated, dried, and fractionated by column chromatography. The fraction containing 2-(4-bromobutyl)-2H-1,4-benzothiazine-3(4H)-one was separated. After crystallization in the presence of diethyl ether, 5.9 g of 2-(4-bromobutyl)-2H-1,4-benzothiazine-3(4H)-one were obtained from this fraction as slightly beige-colored crystals having a melting point of 100° C.

C) A mixture of 3.3 g (=0.011 m) of 2-(4-bromobutyl)-2H-1,4-benzothiazine-3(4H)-one, 3 g (=0.0925 m) of N-[1-(4-fluorophenylmethyl)-1H-benzimidazol-2-yl]-N-(piperidin-4-yl)-amine, and 2.02 g of triethylamine in a mixture of 50 ml toluene and 5 ml dimethylformamide was heated at reflux for 11 hours with stirring.

To work up the reaction mixture it was partially acidified, the solvent was distilled off, and the residue was treated with dichloromethane and aqueous sodium bicarbonate solution. The organic phase was separated and concentrated by distilling off the solvent. The remaining residue was purified by fractional column chromatography. The crude title compound was obtained as an amorphous solid. This was dissolved in isopropanol. Isopropanolic 2.3N hydrochloric acid was added to the isopropanolic solution of the title compound, and the dihydrochloride of the title compound crystallized out. 1.3 g of 2-{4-[4-(N-(1-(4-fluorophenylmethyl)-1H-benzimidazol-2-yl)-amino)-piperidin-1-yl]-butyl}-2H-1,4-benzothiazine-3(4H)-one dihydrochloride were obtained in the form of colorless crystals having a melting point of 206° C.

EXAMPLE 2

2-[3-(4-benzylpiperidin-1-yl)-propyl]-2H-1,4-benzoxazine-3(4H)-one 5.6 g (=0.02 m) of 2-(3-bromopropyl)-2H-1,4-benzoxazine-3(4H)-one prepared analogously to Example 1B starting from 2-aminophenol and 2,5-dibromopentanoyl bromide, 3.86 g (=0.022 m) of 4-benzylpiperidine, and 4.05 g of triethylamine were successively introduced into 70 ml of toluene. The reaction mixture was heated at reflux for 7 hours with stirring. To work up the reaction mixture it was cooled, and 100 ml of aqueous 20% strength hydrochloric acid solution were added. An oily paste was formed which was separated, washed with toluene, and then suspended in a mixture of aqueous sodium bicarbonate solution and dichloromethane. The organic phase was separated, dried over sodium sulfate, and then the solvent was distilled off. The remaining oily residue was fractionated by column chromatography. The title compound obtained in this way was crystallized from 15 ml of ethyl acetate. 6 g of 2-[3-(4-benzylpiperidin-1-yl)-propyl]-2H-1,4-benzoxazine-3(4H)-one were obtained as white crystals having a melting point of 108° C.

EXAMPLE 3

2-[3-(4-benzylpiperidin-1-yl)-propyl]-2H-1,4-benzoxazine-3(4H)-thione.

3 g 0.0082 m) of 2-[3-(4-benzylpiperidin-1-yl)-propyl]-2H-1,4-benzoxazine-3(4H)-one prepared according to Example 2 and 3.91 g of P$_4$S$_4$ in 50 ml of xylene were heated at reflux for one hour with stirring. The mixture was worked up by cooling, separating the resulting precipitate, and introducing the precipitate into a mixture of 100 ml of N sodium hydroxide solution and 150 ml of dichloromethane. The organic phase was separated, and the solvent was distilled off. The crude title compound which remained as a residue was purified by column chromatography. The resulting title compound was dissolved in isopropanol. The dihydrochloride of the title compound was precipitated by adding isopropanolic 2.3N hydrochloric acid solution. 1.3 g of 2-[3-(4-benzylpiperidin-1-yl)-propyl]-2H-1,4-benzoxazine-3(4H)-thione dihydrochloride having a melting point of 210° C. were obtained.

EXAMPLE 4

2-[4-(4-fluorobenzoyl)-piperidin-1-yl]-2H-1,4-benzothiazine-3(4H)-one

A) 0.8 ml (=1 equivalent) of sulfonyl chloride was added dropwise with stirring at room temperature to a suspension of 10.0 mmoles of 2H-1,4-benzothiazine-3(4H)-one in 10 ml of dichloromethane, and the reaction mixture was stirred for a further 5 hours at room temperature. The mixture was worked up by evaporating the solvent to dryness under reduced pressure. The 2-chloro-2H-1,4-benzothiazine-3(4H)-one which remained as a residue (melting point 189°-210° C. with decomposition) was further processed in the next step without additional purification.

B) 7 g (=0.035 m) of 2-chloro-2H-1,4-benzothiazine-3(4H)-one, 7.25 g (=0.035 m) of 4-(4-fluorobenzoyl)-piperidine and 7.1 g of triethylamine in 200 ml of toluene were heated at reflux for 4 hours with stirring. The reaction mixture was worked up by cooling it and then adding 200 ml of toluene and 200 ml of water. The pH of the mixture was adjusted to pH 7 by adding 0.1N hydrochloric acid solution. The organic phase was separated, washed with 200 ml of water, and the solvent was distilled off. The title compound was recovered from the remaining oily residue by fractional column chromatography, crystallized from ethyl acetate, and recrystallized in an ethanol/diethyl ether mixture. 1.95 g of 2-[4-(4-fluorobenzoyl)-piperidin-1-yl]-2H-1,4-benzothiazine-3(4H)-one were obtained as a colorless crystalline powder having a melting point of 218° C.

EXAMPLE 5

4-methyl-2-[4-(4-phenyl-1,2,3,6-tetrahydropyridin-1-yl)-butyl]-2H-1,4-benzothiazine-3(4H)-one 2.4 g (=0.0076 m) of 2-(4-bromobutyl)-4-methyl-2H-1,4-benzothiazine-3(4H)-one, 1.49 g (=0.0076 m) of 4-phenyl-1,2,3,6-tetrahydropyridine hydrochloride and 3.09 g of triethylamine were introduced into 20 ml of toluene. The resulting suspension was heated for 10.5 hours with stirring. The mixture was worked up by cooling and introducing the suspension into 30 ml of 20% strength aqueous hydrochloric acid solution. The resulting precipitate was filtered out, and the aqueous phase was rendered alkaline and extracted with 200 ml of dichloromethane. The precipitate was introduced into an aqueous alkaline solution and extracted with 450 ml of dichloromethane. The combined dichloromethane extracts were washed, dried over sodium sulfate, and the solvent was distilled off. 2.1 g of 4-methyl-2-[4-(4-phenyl-1,2,3,6-tetrahydropyridin-1-yl)-butyl]-2H-1,4-benzothiazine-3(4H)-one were obtained as a beige-colored powder.

EXAMPLE 6

4-methyl-2-[4-(4-phenyl-1,2,3,6-tetrahydropyridin-1-yl)-butyl]-2H-1,4-benzothiazine-3(4H)-one 1.77 g (=0.004 m) of 2-[4-(4-phenyl-1,2,3,6-tetrahydropyridin-1-yl)-butyl]-2H-1,4-benzothiazine-3(4H)one (see Example 10) prepared analogously to Example were dissolved in 20 ml of anhydrous dimethylformamide with stirring. 0.121 g of sodium hydride was added under a nitrogen atmosphere, and the resulting suspension was maintained at room temperature for 10 minutes. 0.70 g of methyl iodide was then added all at once, and the reaction mixture was stirred for 2.5 hours at room temperature. The reaction mixture was worked up by distilling off the solvent, adding 100 ml of water to the residue, and extracting the mixture with 100 ml of ethyl acetate. The organic phase was concentrated by evaporating the solvent, and the crude title compound which remained as a residue was purified by column chromatography. 0.6 g of 4-methyl-2-[4-(4-phenyl-1,2,3,6-tetrahydropyridin-1-yl)-butyl]-2H-1,4-benzothiazine-3(4H)-one was obtained as beige-colored powder.

EXAMPLE 7

7-hydroxy-2-(4-[4-(4-fluorobenzoyl)-piperidin-1-yl]-butyl}-2H-1,4-benzothiazine-3(4H)-one 675 mg (=0.0015 m) of 7-methoxy-2-(4-[4-(4-fluorobenzoyl)-piperidin-1-yl]-butyl)-2H-1,4benzothiazine-3(4H)-one (see Example 18) prepared analogously to Example 4 were placed in 5 ml of dichloromethane with exclusion of moisture. After cooling to −5° C. a solution of 1.10 g of boron tribromide in 1 ml of methylene chloride was added dropwise with stirring. Stirring was then continued for a further 30 minutes at room temperature. The reaction mixture was worked up by adding it with stirring to a mixture of ice and aqueous sodium hydrogen carbonate solution. 200 ml of chloroform were then added. The resulting organic solution was washed with water, dried over sodium sulfate, filtered, and concentrated under reduced pressure. The title compound was obtained from the remaining residue by fractional column chromatography. The fractions containing the title compound were concentrated and treated with ether. 55 mg of 7-hydroxy-2-{4-[4-(4-fluorobenzoyl)-piperazin-1-yl]-butyl}-2H-1,4-benzothiazine-3(4H)-one were obtained.

The compounds of formula I listed in the following Table I were also obtained following the procedures described in the foregoing examples.

EXAMPLE I

Tablets containing
2-(4-[4-(N-(1-(4-fluorophenylmethyl)-1H-benzimidazol-2-yl)-amino)-piperidin-1-yl]-butyl)-2H-1,4-benzothiazine-3(4H)-one Tablets were produced having the following composition per tablet:

| | |
|---|---|
| 2-{4-[4-(N-(1-(4-fluorophenylmethyl)-1H-benzimidazol-2-yl)-amino)-piperidin-1-yl]-butyl}-2H-1,4-benzothiazine-3(4H)-one | 20 mg |
| Corn starch | 60 mg |
| Lactose | 135 mg |
| Gelatine (10 % strength solution) | 6 mg |

The active ingredient, the corn starch and the lactose were mixed with the 10% strength gelatine solution to form a paste. The paste was comminuted, and the resulting granules were placed on a suitable plate and dried at 45° C. The dried granules were passed through a comminuting machine and mixed with the following further adjuvants in a mixer:

| | |
|---|---|
| Talcum | 5 mg |
| Magnesium stearate | 5 mg |
| Corn starch | 9 mg | and then pressed to form 240 mg tablets.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A compound corresponding to the formula I

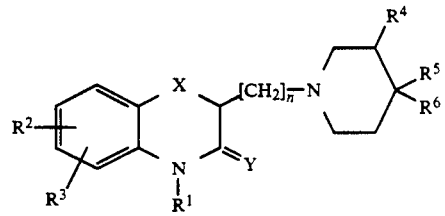

TABLE I

| Ex. | $R^1$ | $R^2$ | $R^3$ | X | Y | n | $R^4$ | $R^5$ | $R^6$ | Salt form | M.p. in °C. |
|---|---|---|---|---|---|---|---|---|---|---|---|
| 8 | H | H | H | S | O | 3 | H | H | im-NH— | 3.HCl.H₂O | 220 |
| 9 | H | H | H | O | O | 4 | H | H | ph- | Base | 160 |
| 10 | H | H | H | S | O | 4 | bon | | ph- | HCl | 220 |
| 11 | H | H | H | S | O | 4 | H | OH | ph- | Base | 138 |
| 12 | H | H | H | O | O | 4 | bon | | ph- | Base | 148 |
| 13 | H | H | H | O | O | 4 | H | OH | ph- | HCl | 176 |
| 14 | H | 6-Cl | H | O | O | 3 | H | CN | ph- | Base | 131 |
| 15 | H | H | H | S | O | 4 | H | CN | ph- | Base | 154 |
| 16 | H | H | H | S | O | O | H | H | ph-CH₂— | Base | 145–148 |
| 17 | H | 7-F— | H | S | O | 4 | bon | | ph- | Base | 152 |
| 18 | H | 7-CH₃O— | H | S | O | 4 | H | H | 4-F-pH-CO— | Base | am |
| 19 | H | 6-CH₃— | 7-CH₃— | S | O | 4 | bon | | ph- | Base | 153 |
| 20 | H | 7-Cl | H | S | O | 4 | H | H | im-NH— | 2.HCl | 160 |
| 21 | H | H | H | S | O | 3 | H | H | ph-CH₂— | Base | 114 | im = 1-(4-fluorophenylmethyl)-1H-benzimidazol-2-yl, ph = phenyl, bin = bond, HCl = hydrochloride, Base = free base, am = amorphous.

wherein

X is oxygen or sulfur,

Y is oxygen or sulfur $R^1$ is hydrogen or lower alkyl, $R^2$ is hydrogen, lower alkyl, halogen, lower alkoxy, hydroxy, nitro or trifluoromethyl, and $R^3$ is hydrogen, lower alkyl, halogen or lower alkoxy, or $R^2$ and $R^3$ are bonded to adjacent carbon atoms and together form an alkylenedioxy group having 1-2 carbon atoms, n is an integer from 0 to 4, $R^4$ is hydrogen, and $R^5$ is hydrogen, hydroxy or cyano, or $R^4$ and $R^5$ together form a bond, $R^6$ is an A—$R^7$ group, wherein $R^7$ is a phenyl group substituted by 0 to 3 substituents selected from the group consisting of lower alkyl, lower alkoxy, halogen and trifluoromethyl, and A is a —$CH_2$— group, a CO group or a bond, or $R^6$ is a group corresponding to the formula a

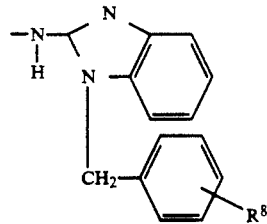

wherein $R^8$ is halogen,
and physiologically acceptable acid addition salts thereof.

2. A compound according to claim 1, wherein Y is oxygen.

3. A compound according to claim 1, wherein n is 3 or 4.

4. A compound according to claim 1, wherein $R^1$ is hydrogen.

5. A compound according to claim 1, wherein $R^2$ is hydrogen or lower alkyl, and $R^3$ is hydrogen.

6. A compound according to claim 1, wherein $R^4$ is hydrogen.

7. A compound according to claim 1, wherein Y is oxygen, $R^1$ is hydrogen, $R^2$ is hydrogen or lower alkyl, $R^3$ is hydrogen, n is 3 or 4, $R^4$ and $R^5$ each is hydrogen or together form a bond, and $R^6$ represents a benzyl, benzoyl or phenyl group optionally substituted by lower alkyl, lower alkoxy or halogen, or $R^6$ represents the group a.

8. A compound according to claim 7, wherein X is sulfur, $R^2$, $R^4$ and $R^5$ each is hydrogen, and $R^6$ is a 1-(4-fluorophenylmethyl)-1H-benzimidazol-2-yl group.

9. A pharmaceutical composition comprising an effective anti-inflammatory or anti-allergic amount of a compound according to claim 1, and a conventional pharmaceutical carrier or adjuvant.

* * * * *